US00PP29442P3

(12) United States Plant Patent
Vissers et al.

(10) Patent No.: US PP29,442 P3
(45) Date of Patent: Jul. 3, 2018

(54) STRAWBERRY PLANT NAMED 'P061103V'

(50) Latin Name: ***Fragaria* x *ananassa***
Varietal Denomination: P061103V

(71) Applicants: Gerardus Theodorus Maria Vissers, America (NL); Hubertus Antonius Maria Konings, America (NL); Johannes Theodorus Albert Marie Obers, America (NL)

(72) Inventors: Gerardus Theodorus Maria Vissers, America (NL); Hubertus Antonius Maria Konings, America (NL); Johannes Theodorus Albert Marie Obers, America (NL)

(73) Assignee: Vissers America B.V., America (NL)

( * ) Notice: Subject to any disclaimer, the term of this patent is extended or adjusted under 35 U.S.C. 154(b) by 0 days.

(21) Appl. No.: 14/999,473

(22) Filed: May 11, 2016

(65) Prior Publication Data

US 2017/0332533 P1 Nov. 16, 2017

(51) Int. Cl.
*A01H 5/08* (2018.01)

(52) U.S. Cl.
USPC ..... Plt./209
CPC ..... *A01H 5/0893* (2013.01)

(58) Field of Classification Search
USPC ..... Plt./208, 209
See application file for complete search history.

(56) References Cited

PUBLICATIONS

UPOV hit on Strawberry plant named 'P061103v', CA PBR 16-8977, application date Jul. 15, 2015.*
Poland Plants, Harmony"P061103V", downloaded from http://www.polandplants.pl/de/Truskawki/Opis-odmian/Odmianypowtarzajace/Harmony-R-P061103V, May 22, 2014.*
Google page showing search results for "erdbeer p061103v" that were published prior to May 11, 2015, downloaded on Aug. 4, 2017.*

* cited by examiner

*Primary Examiner* — Anne Marie Grunberg
(74) *Attorney, Agent, or Firm* — C. A. Whealy

(57) ABSTRACT

A new and distinct cultivar of Strawberry plant named 'P061103V', characterized by its semi-upright plant habit; moderately vigorous to vigorous growth habit; uniform fruit ripening; large conical fruits that are glossy and bright red in color with seeds positioned below the surface; pleasant fruit aroma and taste; good fruit postharvest longevity; long flowering and fruit harvesting period; low susceptibility to *Podosphaera aphanis* (powdery mildew) and *Phytophthora cactorum* and low level of attractiveness to mites and thrips.

6 Drawing Sheets

Botanical designation: *Fragaria* x *ananassa*.
Cultivar denomination: 'P061103V'.

BACKGROUND OF THE INVENTION

The present Invention relates to a new and distinct cultivar of Strawberry plant, botanically known as *Fragaria* x *ananassa* and hereinafter referred to by the name 'P061103V'.

The new Strawberry plant is a product of a planned breeding program conducted by the Inventors in America, The Netherlands. The objective of the breeding program was to develop new early-ripening Strawberry plants with good fruit quality, ease of harvesting, good postharvest longevity and resistance to pathogens.

The new Strawberry plant originated from a cross-pollination in May, 2009 in America, The Netherlands of two unnamed proprietary selections of *Fragaria* x *ananassa*, not patented. The new Strawberry plant was discovered and selected by the Inventors as a single plant from within the progeny of the stated cross-pollination in a controlled environment in America, The Netherlands in August, 2011.

Asexual reproduction of the new Strawberry plant by vegetative cuttings in a controlled environment at America, The Netherlands since 2011, has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'P061103V'. These characteristics in combination distinguish 'P061103V' as a new and distinct Strawberry plant:

1. Semi-upright plant habit.
2. Moderately vigorous to vigorous growth habit.
3. Uniform fruit ripening.
4. Large conical fruits that are glossy and bright red in color with seeds positioned below the surface.
5. Pleasant fruit aroma and taste.
6. Good fruit postharvest longevity.
7. Long flowering and fruit harvesting period.

8. Low susceptibility to *Podosphaera aphanis* (powdery mildew) and *Phytophthora cactorum* and low level of attractiveness to mites and thrips.

Plants of the new Strawberry differ primarily from plants of the female parent selection in fruit taste and fruits of plants of the new Strawberry are more flavorful than fruits of plants of the female parent selection.

Plants of the new Strawberry differ primarily from plants of the male parent selection in pathogen susceptibility as plants of the new Strawberry have low susceptibility to *Podosphaera aphanis* whereas plants of the male parent selection are susceptible to *Podosphaera aphanis*.

Plants of the new Strawberry can be compared to plants of *Fragaria* x *ananassa* 'Selva', disclosed in U.S. Plant Pat. No. 5,266. In side-by-side comparisons, plants of the new Strawberry differ primarily from plants of 'Selva' in the following characteristics:

1. Plants of the new Strawberry are larger than plants of 'Selva'.
2. Plants of the new Strawberry flower earlier than plants of 'Selva'.
3. Fruits of plants of the new Strawberry ripen earlier than fruits of plants of 'Selva'.
4. Fruits of plants of the new Strawberry are larger than fruits of plants of 'Selva'.
5. Fruits of plants of the new Strawberry are more uniform in shape than fruits of plants of 'Selva'.
6. Fruits of plants of the new Strawberry are glossier than fruits of plants of 'Selva'.
7. Fruits of plants of the new Strawberry are more flavorful than fruits of plants of 'Selva'.
8. Fruits of plants of the new Strawberry have seeds positioned below the surface whereas fruits of plants of 'Selva' have seeds positioned at the surface level.
9. Plants of the new Strawberry produce more fruits per plant than plants of 'Selva'.
10. Fruits of plants of the new Strawberry are heavier than fruits of plants of 'Selva'.

Plants of the new Strawberry can be compared to plants of *Fragaria* x *ananassa* 'Albion', not patented. In side-by-side comparisons, plants of the new Strawberry differ primarily from plants of 'Albion' in the following characteristics:

1. Fruits of plants of the new Strawberry ripen earlier than fruits of plants of 'Albion'.
2. Fruits of plants of the new Strawberry are more conical than fruits of plants of 'Albion'.
3. Fruits of plants of the new Strawberry are not as dark red as fruits of plants of 'Albion'.
4. Fruits of plants of the new Strawberry have seeds positioned below the surface whereas fruits of plants of 'Albion' have seeds positioned at the surface level.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet is a side perspective view of a typical flowering and fruiting plant of 'P061103V' grown in trays.

The photograph on the second sheet is a close-up view of typical fully opened flowers of 'P061103V'.

The photograph on the third sheet is a close-up view of typical developed fruits of 'P061103V'.

The photograph on the fourth sheet is a close-up view of the lower surface of a typical leaf of 'P061103V'.

The photograph on the fifth sheet is a close-up view of the lower surface of a typical flower of 'P061103V'.

The photograph on the sixth sheet comprises longitudinal cross-sectional views of typical fruits of 'P061103V'.

DETAILED BOTANICAL DESCRIPTION

The aforementioned photographs, following observations and measurements describe plants grown in 200-cc trays during the spring, summer and autumn in a glass-covered greenhouse in America, The Netherlands and under cultural practices typical of commercial Strawberry production. During the production of the plants, day temperatures ranged from 15° C. to 25° C. and night temperatures ranged from 7° C. to 14° C. Plants were one year old when the photographs and description were taken. In the following description, color references are made to The Royal Horticultural Society Colour Chart, 2001 Edition, except where general terms of ordinary dictionary significance are used.

Botanical classification: *Fragaria* x *ananassa* 'P061103V'.

Parentage:

*Female, or seed, parent*.—Unnamed proprietary selection of *Fragaria* x *ananassa*, not patented.

*Male, or pollen, parent*.—Unnamed proprietary selection of *Fragaria* x *ananassa*, not patented.

Propagation:

*Type*.—By vegetative cuttings.

*Time to initiate roots, summer*.—About one to four days at soil temperatures about 15° C.

*Time to produce a rooted young plant, summer*.—About four weeks at soil temperatures ranging from 18° to 20° C.

*Root description*.—Medium in thickness, fibrous; typically cream to white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Perennial; compact and semi-upright plant habit; leaves basal; moderately vigorous to vigorous growth habit; moderate growth rate; fairly densely foliated and open canopy.

*Plant height*.—About 20 to 40 cm.

*Plant diameter*.—About 30 to 50 cm.

*Stolon texture*.—Moderately pubescent.

*Stolon color*.—Close to 145A.

Leaf description:

*Arrangement and appearance*.—Basal rosette; compound with typically three or four leaflets per leaf; leaves non-variegated.

*Leaflet length*.—About 10 to 13 cm.

*Leaflet width*.—About 9 to 12 cm.

*Leaflet shape*.—Broadly ovate; terminal leaflet, flat to concave.

*Leaflet apex*.—Obtuse, emarginate.

*Leaflet base*.—Obtuse to rounded.

*Leaflet margin*.—Crenate.

*Leaflet texture and luster, upper surface*.—Smooth, glabrous; no blistering; moderately glossy.

*Leaflet texture and luster, lower surface*.—Pubescent, rough; matte.

*Leaflet venation*.—Pinnate.

*Leaflet color*.—Developing leaflets, upper surface: Close to 137A. Developing leaflets, lower surface: Close to 138A. Fully expanded leaflets, upper surface: Close to between 137A and 139A; venation, close to 144C. Fully expanded leaflets, lower surface: Close to 138A; venation, close to 144C.

*Stipule color*.—If developed, close to 137A occasionally tinged with close to 187A.

*Petioles*.—Length: About 15 to 20 cm. Diameter: About 2.5 to 6 mm. Texture, upper and lower surfaces: Pubescent; attitude of hairs, horizontal. Color, upper and lower surfaces: Close to 145A.

Flower description:

*Flower form and flowering habit*.—Rotate flowers arranged singly at lateral apices; flowers held at the foliar plane; about 20 to 50 flowers developing per plant; flowers are self-fertile.

*Fragrance*.—None detected.

*Natural flowering season*.—Long flowering period; plants flower in late April to early November in The Netherlands.

*Flower diameter*.—About 2 to 3 cm.

*Flower depth* (*height*).—About 8 mm to 12 mm.

*Petals*.—Arrangement: Single whorl of six or seven petals; petals slightly imbricate. Length: About 8 mm to 12 mm. Width: About 8 mm to 10 mm. Shape: Round to broadly ovate. Apex: Rounded. Base: Attenuate. Margin: Entire. Texture, upper and lower surfaces: Smooth, glabrous; satiny. Color: When opening and fully opened, upper surface: Close to 155D. When opening and fully opened, lower surface: Close to 155D.

*Sepals*.—Arrangement and calyx description: Single whorl of ten to twelve sepals; calyx, star-shaped; calyx adherence is weak to moderate; sepal attachment is inserted; sepals are orientated upwards from the fruit. Calyx diameter: About 3 cm to 6 cm. Length: About 8 mm to 14 mm. Width: About 3 mm to 5 mm. Shape: Lanceolate to ovate. Apex: Acute. Base: Fused. Margin: Entire. Texture, upper and lower surfaces: Smooth, glabrous. Color, upper and lower surfaces: Close to 137A.

*Peduncles*.—Length: About 5 cm to 10 cm. Diameter: About 1 mm to 2 mm. Strength: Strong. Texture: Pubescent. Color: Close to 144B.

*Pedicels*.—Length: About 3 cm to 8 cm. Diameter: About 1 mm to 3 mm. Strength: Strong. Texture: Smooth, glabrous. Color: Close to 144B.

*Reproductive organs*.—Stamens: Quantity per flower: About 25. Anther length: About 3 mm. Anther shape: Lanceolate to elliptic. Anther color: Close to 8A. Pollen amount: Abundant. Pollen color: Close to 6A. Pistils: Quantity per flower: More than 250. Pistil length: About 1 mm to 2 mm. Stigma shape: Rounded. Stigma color: Close to 5A. Fruits: Quantity per truss: About six to nine. Natural fruiting season: Relatively early and long fruiting season, fruits fully ripen in about four weeks and plants develop fruit from May until November in The Netherlands; fruiting is remontant. Postharvest longevity: About seven days at 4° C. Length: About 4 cm to 5 cm. Diameter: About 2 cm to 4 cm. Cavity length: About 1.5 cm. Cavity width: About 5 mm. Shape: Conical; secondary fruits are occasionally more carved distally. Fruit weight per fruit, first quality: About 18 g to 22 g. Fruit weight per plant, first quality: About 2,000 g. Firmness: Firm. Fragrance, taste: Pleasant; good balance between sweetness and acidity. Sweetness: About 7 Brix. Luster: Uniformly glossy. Surface unevenness: Smooth. Color, surface: Close to 43A. Color, flesh: Close to 40A. Color, core: Close to 43C. Seed density: Medium. Quantity of achenes per fruit: About 300 to 350. Achene position: Positioned below then surface, slightly indented; width of band without achenes, about 1.5 mm to 2 mm. Achene color: Close to 32A.

Disease and pest resistance: Plants of the new Strawberry have been observed to have low susceptibility to *Podosphaera aphanis* (formerly known as *Sphaerotheca macularis*) and *Phytophthora cactorum*. Plants of the new Strawberry have also been observed to have a low level of attractiveness to mites and thrips.

It is claimed:

1. A new and distinct Strawberry plant named 'P061103V' as illustrated and described.

* * * * *

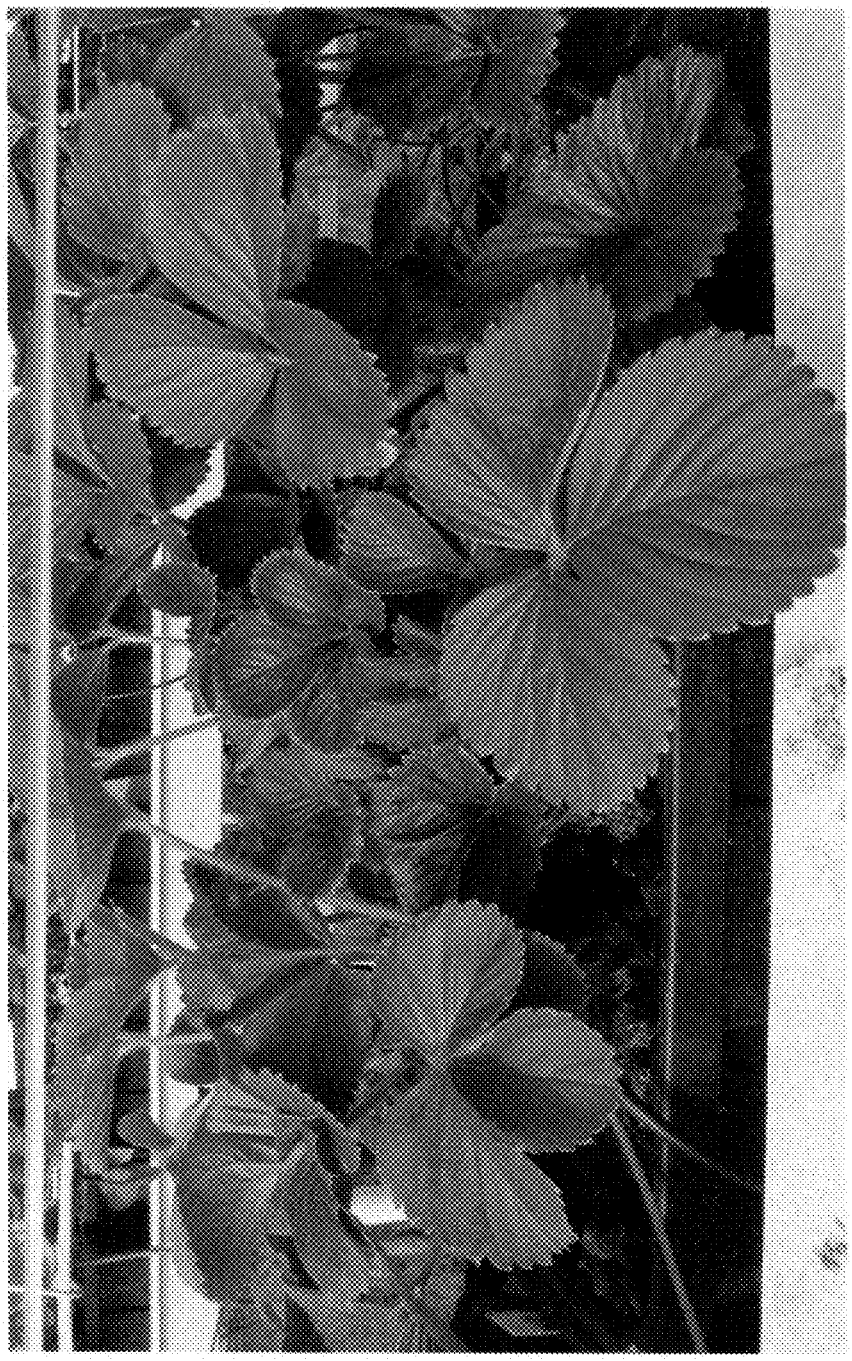

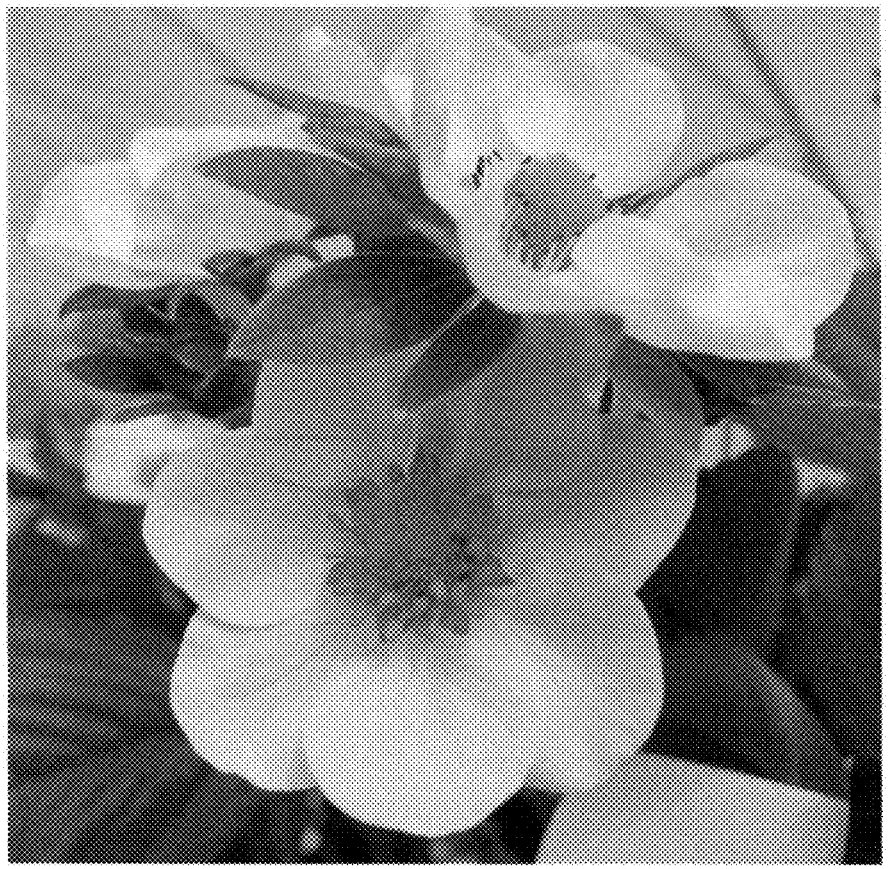

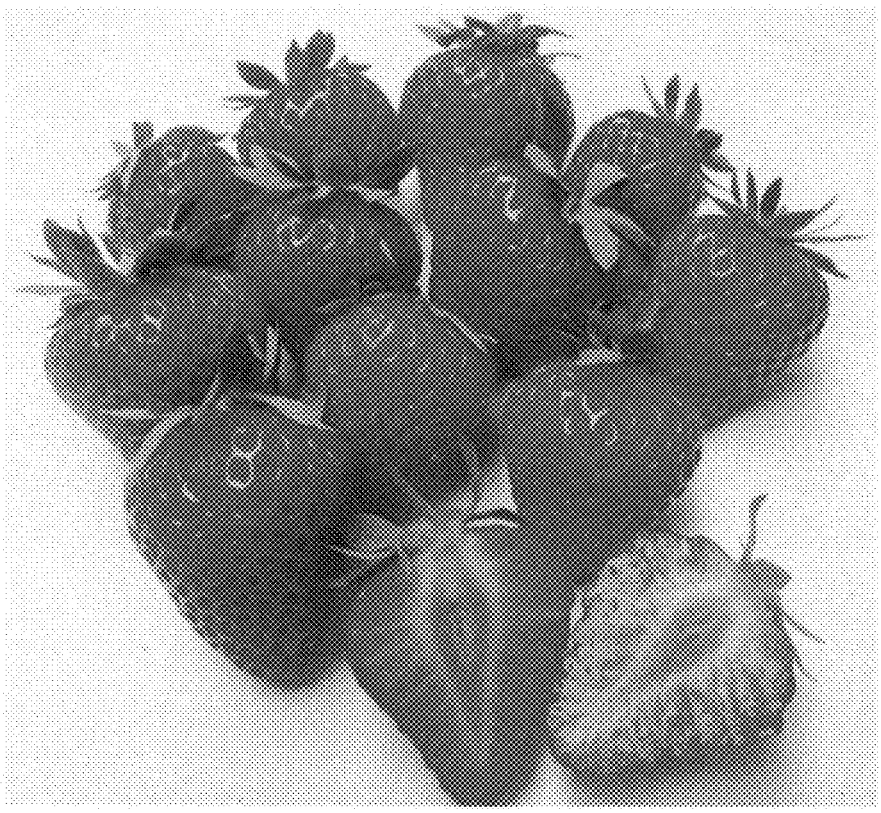

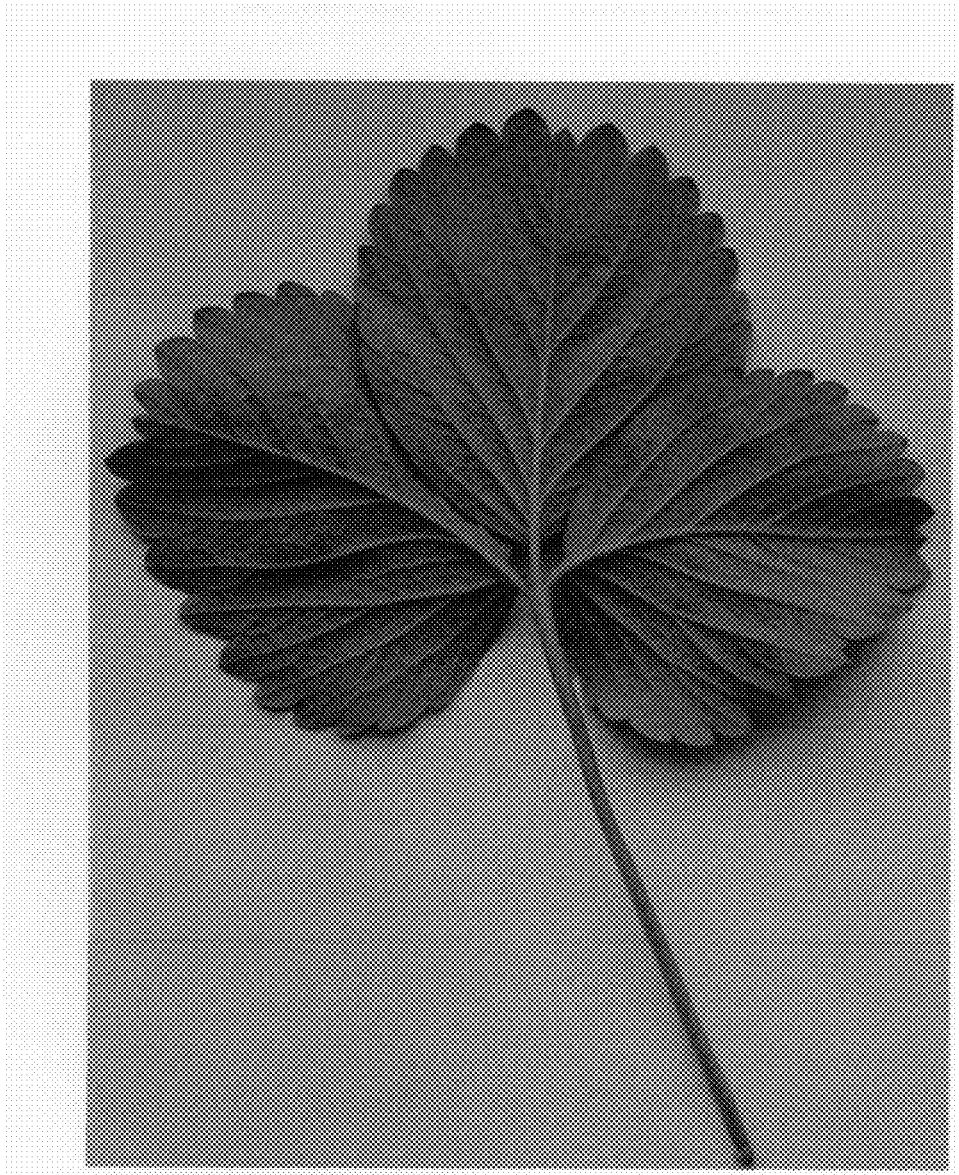

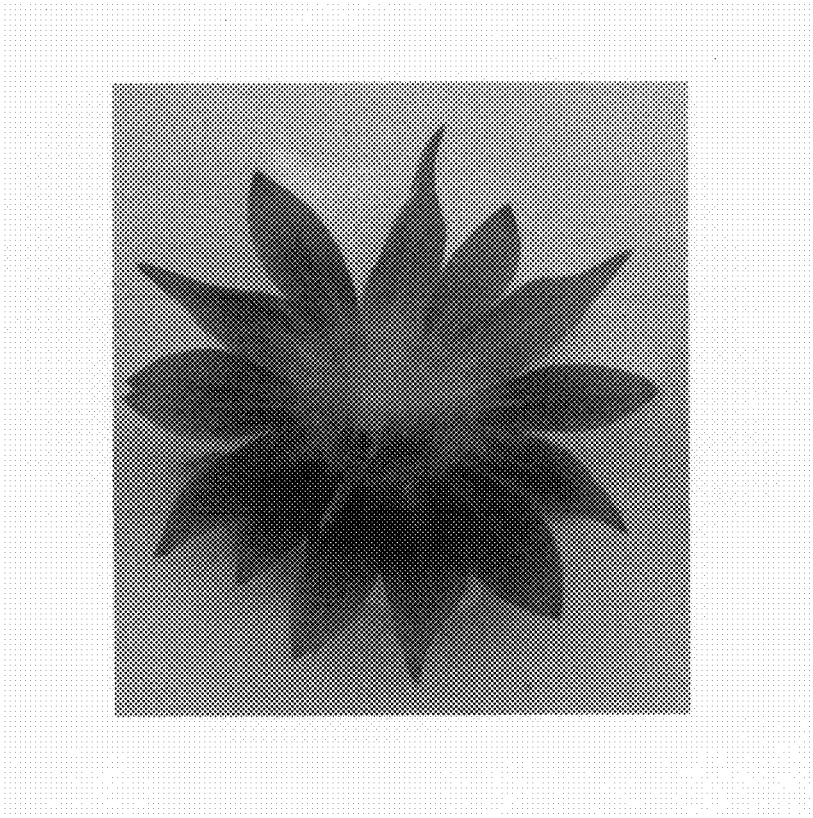

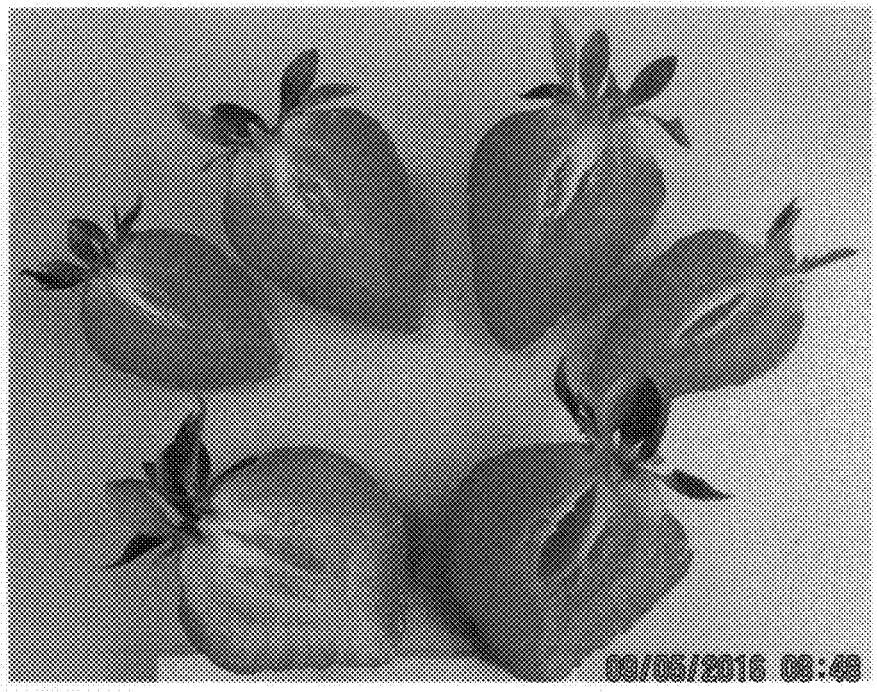
09/05/2015 08:48